United States Patent
Frauenfeld et al.

(10) Patent No.: US 9,474,646 B2
(45) Date of Patent: Oct. 25, 2016

(54) MEDICAL TOOL AND METHOD FOR PRODUCING A MEDICAL TOOL

(75) Inventors: Dieter Frauenfeld, Heidelberg (DE); Rene Draheim, Sandhausen (DE)

(73) Assignee: GEUDER AG, Heidelberg (DE)

( * ) Notice: Subject to any disclaimer, the term of this patent is extended or adjusted under 35 U.S.C. 154(b) by 341 days.

(21) Appl. No.: 14/130,468

(22) PCT Filed: Jul. 11, 2012

(86) PCT No.: PCT/DE2012/200046
§ 371 (c)(1),
(2), (4) Date: Dec. 31, 2013

(87) PCT Pub. No.: WO2013/007255
PCT Pub. Date: Jan. 17, 2013

(65) Prior Publication Data
US 2014/0128879 A1 May 8, 2014

(30) Foreign Application Priority Data

Jul. 13, 2011 (DE) .......................... 10 2011 107 676

(51) Int. Cl.
*A61F 9/00* (2006.01)
*A61F 9/007* (2006.01)
*A61B 17/32* (2006.01)
*A61B 17/00* (2006.01)

(52) U.S. Cl.
CPC .......... *A61F 9/00745* (2013.01); *A61B 90/92* (2016.02); *A61B 2017/0023* (2013.01); *A61B 2017/00464* (2013.01); *A61B 2017/32008* (2013.01); *A61B 2090/0814* (2016.02); *A61F 9/00736* (2013.01)

(58) Field of Classification Search
CPC .......... A61F 9/00736; A61F 9/00745; A61B 2017/32008
See application file for complete search history.

(56) References Cited

U.S. PATENT DOCUMENTS 4,926,885 A 5/1990 Hinkle
5,830,192 A 11/1998 Van Voorhis
(Continued)

FOREIGN PATENT DOCUMENTS

DE 102008023967 A1 11/2009
DE 102008060868 A1 6/2010
(Continued)

OTHER PUBLICATIONS

International Searching Authority, International Search Report (ISR) and Written Opinion for International Application No. PCT/DE2012/200046, mailed Nov. 8, 2012, 18 pages, European Patent Office, The Netherlands.
(Continued)

*Primary Examiner* — Robert Lynch
(74) *Attorney, Agent, or Firm* — Alston & Bird LLP

(57) ABSTRACT

A hollow needle for an instrument used in ocular surgery for the in-vivo disintegration of organic lenses via ultrasound, having a functional part (1) and a connector part (2), with the connector part (2) having handling portions(3) and serving to attach the tool in a removable fashion to a handle, wherein the properties of the handling portions (3) change upon connection of the tool to the handle, removal of the tool from the handle, and/or upon reprocessing of the tool. In addition, a method is disclosed for the production of a corresponding medical tool.

19 Claims, 3 Drawing Sheets

(56) References Cited

U.S. PATENT DOCUMENTS

Figure 1:
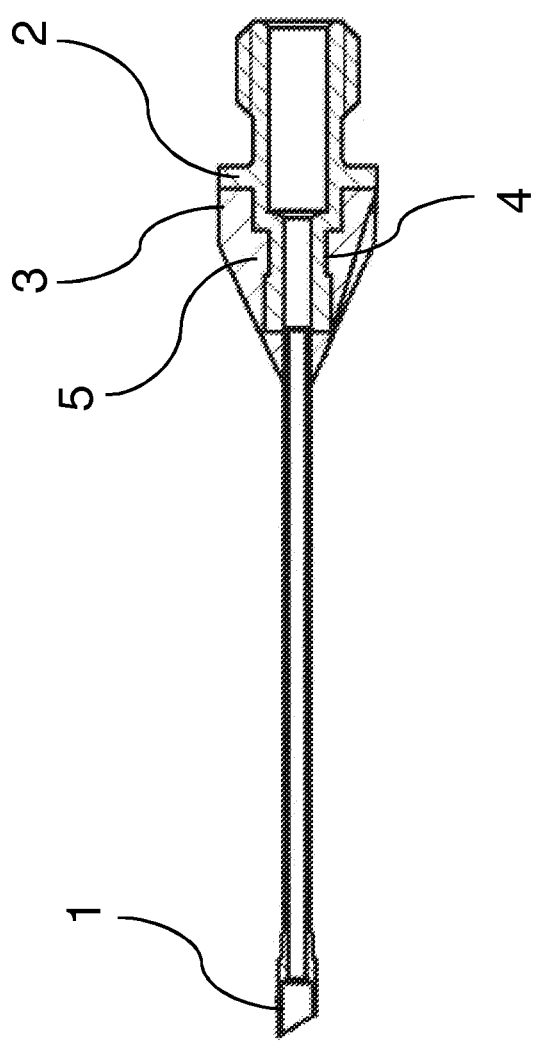

| | | |
|---|---|---|
| 6,575,919 B1 | 6/2003 | Reiley et al. |
| 2003/0171681 A1 | 9/2003 | Weilandt |
| 2006/0054525 A1 | 3/2006 | Dean et al. |
| 2007/0197935 A1* | 8/2007 | Reiley ............... A61B 17/3417 600/567 |
| 2008/0188792 A1* | 8/2008 | Barrett ............... A61F 9/00745 604/22 |
| 2010/0217336 A1 | 8/2010 | Crawford et al. |
| 2010/0261967 A1 | 10/2010 | Pacey et al. |
| 2011/0295192 A1 | 12/2011 | Geuder |
| 2012/0016292 A1 | 1/2012 | Goldberg et al. |

FOREIGN PATENT DOCUMENTS

| | | |
|---|---|---|
| DE | 102008061362 A1 | 6/2010 |
| EP | 1925261 A1 | 5/2008 |
| WO | WO 98/37819 A1 | 9/1998 |
| WO | WO 01/62153 A1 | 8/2001 |
| WO | WO 2010/111611 A2 | 9/2010 |

OTHER PUBLICATIONS

The International Bureau of WIPO, Advance E-mail Transmitting the International Preliminary Report on Patentability (English translation of the Written Opinion) for International Application No. PCT/DE2012/200046, mailed Jan. 23, 2014, 15 pages, Switzerland.

* cited by examiner

MEDICAL TOOL AND METHOD FOR PRODUCING A MEDICAL TOOL

CROSS REFERENCE TO RELATED APPLICATIONS

This application is a national stage application, filed under 35 U.S.C. §371, of International Application No. PCT/DE2012/200046, filed Jul. 11, 2012, and German Application No. 10 2011 107 676.3, filed Jul. 13, 2011, all of which are hereby incorporated by reference in their entirety.

BACKGROUND

1. Technical Field

The invention relates to a medical tool, particularly a hollow needle for an instrument used in ocular surgery for the in-vivo disintegration of organic lenses by means of ultrasound, having a functional part and a connector part, with the connector part having handling means and serving to provide a removable connection to a handle. The invention further relates to a method for the production of such a medical tool.

2. Description of Related Art

Medical tools of the type under discussion have been known in practice for years. Concretely, such a medical tool may be, for example, an ultrasound-activated hollow needle for an ocular surgery instrument. Purely by way of example, we refer here to DE 10 2008 023 967 A1.

Ultrasound-activated hollow needles are used in cataract operations in the field of ocular surgery for the purpose of disintegrating lenses. To this end, the free end of the hollow needle—the functional part—is placed in high-frequency axial motion and moved directly toward the cataract. Ultrasound waves are emitted by the functional part in order to emulsify the tissue. Lens debris is suctioned off by the hollow needle along with a liquid supplied to the eye.

Before the operation, the medical tool must be connected to a handle via a connector part. If the hand-held medical equipment is an ultrasound-activated hollow needle for use in ocular surgery, said needle is connected to a handle that causes the functional part to oscillate and that suctions off lens debris. It is further known from the prior art for the connector part of the tool to have handling means. In order to connect the tool to the handle in the simplest manner possible, it may be gripped on the handling means. The handling means are embodied in an integral fashion with the connector part.

In order for the patient to recover after the surgery as quickly as possible, the attempt is made to conduct the intervention with a low level of trauma. Here, we wish to refer by way of example to the hollow needles used in ocular surgery, which are designed to be extremely small, with the trend in development moving toward ever-smaller dimensions and smaller lumens of the tools and hollow needles. However, it is problematic that tools that have already been used once cannot be reliably prepared or sterilized because their small dimensions and lumens. Therefore, patients are subjected to the realistic risk of cross-contamination if the tool has already been used and subsequently not correctly sterilized. Infections such as, for example, hepatitis or HIV may be transmitted in this manner.

Another problem lies in the fact that material fatigue occurs in the tools due to the small dimensions that, in an extreme case, may even cause the tool to break. Safely using tools that are placed into oscillation—such as, for example, hollow needles used in ocular surgery—multiple times is therefore not possible. The risk of injury to the patient is too high in the case of multiple uses of preprocessed tools.

BRIEF SUMMARY

The object of the present invention is therefore to design and refine a medical tool of the type mentioned at the outset in such a way that, when handled in a simple fashion, safe functioning for the patient is guaranteed and the danger of cross-contamination is minimized. The further object of the invention is to provide a method for the production of such a medical tool.

The object stated above is attained according to the invention by the features of Claim 13. According to Claim 13, the medical tool under discussion is characterized in that the properties of the handling means change when connecting the tool to the handle and releasing the tool from the handle and/or when reprocessing the tool.

With regard to the method according to the invention, the object stated above is attained by the features of Claim 24. According to Claim 24, the method according to the invention is characterized in that the handling means are attached to the finished connector part by injection molding or by a three-dimensional pressure method.

The inventors recognized that the fundamental object can be attained in a surprisingly simple fashion by a clever design of the handling means. To this end, the handling means are designed in such a way that the properties of the handling means change upon connecting the tool to the handle or releasing the tool from the handle or when reprocessing the tool. Here, it should be noted that the term "properties" should be understood in its broadest sense, including any property of the handle that is perceptible to the user of the medical tool. This structure of the handling means obviates undesired multiple uses of the tool in an astoundingly simple manner. Changing the properties of the handle may be caused, for example, by connecting the tool to the handle or releasing the tool from the handle. Thus, it is automatically visible whether the tool has already been used. Moreover, the change to the handle may be caused by a reprocessing of the tool, regardless of the kind of reprocessing. The operator is constantly informed by the properties of the handling means whether the tool may be used for a medical intervention. The risk of infection and injury posed by the medical tool is reduced to a minimum by the design according to the invention.

From a structural viewpoint, it is particularly advantageous for the handling means to at least partially surround the connector part in a radial fashion. It is furthermore advantageous for the handling means to surround the connector part completely, such that the handling means are constantly visible independently of the radial orientation of the tool. Thus, the operator always has an ideal view of the handling means and their properties. A change to the properties is easy for the operator to recognize.

With regard to a secure connection between the handling means and the connector part, it is conceivable for the connector part to comprise a recess and the handling means to comprise a protrusion corresponding to the recess. The recess on the connector part may be embodied, for example, in the shape of a groove extending in the longitudinal direction of the tool. The protrusion of the handling means is then designed in a correspondingly elongated fashion and extends in the recess of the connector part. This structural measure allows the handling means to be disposed on the connector part in a rotationally secure fashion. Moreover, it is conceivable for the handling means to comprise a recess and for the connector part to comprise a protrusion corresponding to the recess. It is also possible for a plurality of recesses and protrusions having any desired geometry to be provided on the connector part and on the handling means. In order to secure the handling means in the longitudinal direction of the tool as well, the recess may be designed, for example, as a groove running around the connector part in a radial fashion.

It is advantageous for the handling means to be designed in such a way that their optical properties change upon processing and/or sterilization. Here, any type of reprocessing or sterilization is conceivable such as, for example, steam sterilization, hot-air sterilization, chemical sterilization, radiosterilizaiton, plasma sterilization, etc. To this end, the handling means may be made of a material that, for example, discernibly changes its color and/or transparency upon reprocessing. Any change to the optical properties of the handling means that is discernible to the operator is conceivable here. During surgical operation, it is thus also simple to determine whether the tool is being used for the first time. Moreover, it is conceivable for the handling means to be coated—for example, lacquered—with a material having the corresponding properties.

Moreover, the handling means can be embodied in such a way that they are damaged with the tool is reprocessed or sterilized. Any type of reprocessing or sterilization is conceivable here such as, for example, steam sterilization, hot-air sterilization, chemical sterilization, radiosterilizaiton, plasma sterilization, etc. For example, the handling means may be made of a material that melts when heated. This allows the operator to easily discern whether the tool has been used and reprocessed or sterilized. It is further conceivable for the handling means to be coated, for example, lacquered, with a material that has the corresponding properties. The use of reprocessed tools and the risks to the patient associated therewith is thus eliminated.

In order to be able to attach the tool to the handle as simply as possible, the handling means may serve as an engagement point for a clamping tool. To this end, the handling means may have a polygonal cross section, for example, the shape of a hexagonal nut. Moreover, the surface of the handling means may have a contour or recesses structured in any desired fashion, such that the clamping tool is able to engage with the handling means.

It is furthermore advantageous for the handling means to be designed in such a way that they are noticeably damaged by the clamping tool when connected to or released from the handle.

In order to simplify handling of the tool, it is particularly advantageous for the handling means to comprise a coding identifying the tool. The coding may be realized, for example, by a certain shape or geometry or a certain color of the handling means. Various geometries or different lumens of the tool may be designated in this manner with very little structural effort. Because these tools are often small, the handling of the tool is considerably simplified by coding the handling means.

It is particularly advantageous for the handling means to influence the oscillation behavior of the tool as an attenuator. If the tool is an instrument for ocular surgery, for example, that is subjected to ultrasound, the oscillation behavior can be influenced in a targeted fashion by the handling means.

The statements made above regarding the medical tool according to the invention also apply to the method according to the invention. To expand upon the statements made above, it should be mentioned that it is advantageous for the handling means to be attached to the finished connector part by injection molding or by means of a three-dimensional pressure method. The tool may, for example, initially be produced by machining or deformation and attached to the connector part and then the handling means. Here, the handling means are produced according to the invention in an injection molding process or by an "accretion" of material on the connector part. This produces a fixed connection between the handling means and the connector part such that the handling means cannot simply be disconnected from the connector part—particularly not without visible damage.

DETAILED DESCRIPTION OF THE DRAWINGS

There are various options for structuring and refining the teaching of the present invention in an advantageous fashion. In this context, we refer on the one hand to the Claims that are dependent upon Claim 1 and on the other hand to the following description of a preferred exemplary embodiment with reference to the drawings. In conjunction with the explanation of the preferred exemplary embodiment of the invention with reference to the drawings, generally preferred structures and refinements of the teaching will also be described. The drawings show FIG. 1 a schematic depiction of an exemplary embodiment of a tool according to the invention in a partially sectioned side view, FIG. 2 a schematic depiction of the tool according to the invention from FIG. 1 in a side view, with the handling means being disconnected from the connector part, and FIG. 3 a schematic depiction of the tool according to the invention from FIG. 1 in a perspective view, with the handling means being disconnected from the connector part.

DETAILED DESCRIPTION OF VARIOUS EMBODIMENTS

FIG. 1 shows a schematic depiction of an exemplary embodiment of a tool according to the invention. Here, the tool is embodied as a hollow needle for an instrument to be used in ocular surgery for the in-vivo disintegration of organic lenses by means of ultrasound. The hollow needle comprises a functional part 1 that is inserted into the eye and placed in high-frequency axial motion in order to disintegrate the lens tissue. Additionally, a connector part 2 is provided by means of which the hollow needle can be connected to a handle in a releasable fashion. The handling means 3 are provided on the connector part 2. The handling means 3 are attached to the connector part 2 in an injection molding process. The properties of the handling means change upon connection of the tool to the handle or removal of the tool from the handle or upon reprocessing of the tool. In order to fix the handling means 3 in the longitudinal direction of the hollow needle, the connector part 2 comprises a first recess 4 into which a first protrusion 5 of the handling means 3 engages.

Figure 2:
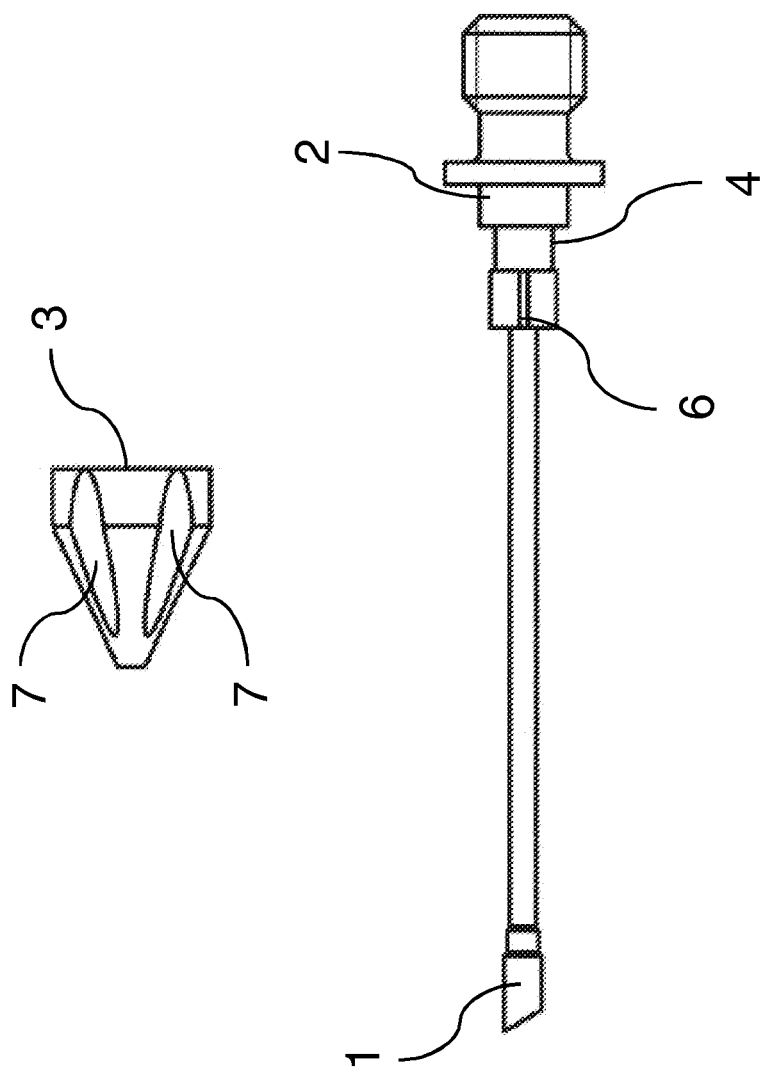

FIG. 2 shows a side view of the tool according to the invention from FIG. 1. In order to show the construction more clearly, the handling means 3 are shown detached from the connector part 2. FIG. 2 clearly shows that the connector part 2 comprises a second recess 6 in the form of a groove. The second recess 6 extends over the connector part 2 in the longitudinal direction. The handling means 3 comprise a protrusion that corresponds with the recess 6. Thus, the handling means 3 are also secured against slippage in a radial direction. Depressions 7 are provided on the surface of the handling means 3 that serve as an engagement point for a clamping tool. The hollow needle can be screwed onto the handle in a fixed manner with the aid of the clamping tool, with the handling means 3 being secured against radial slippage by the second recess 6 and the corresponding protrusion of the handling means 3.

Figure 3:
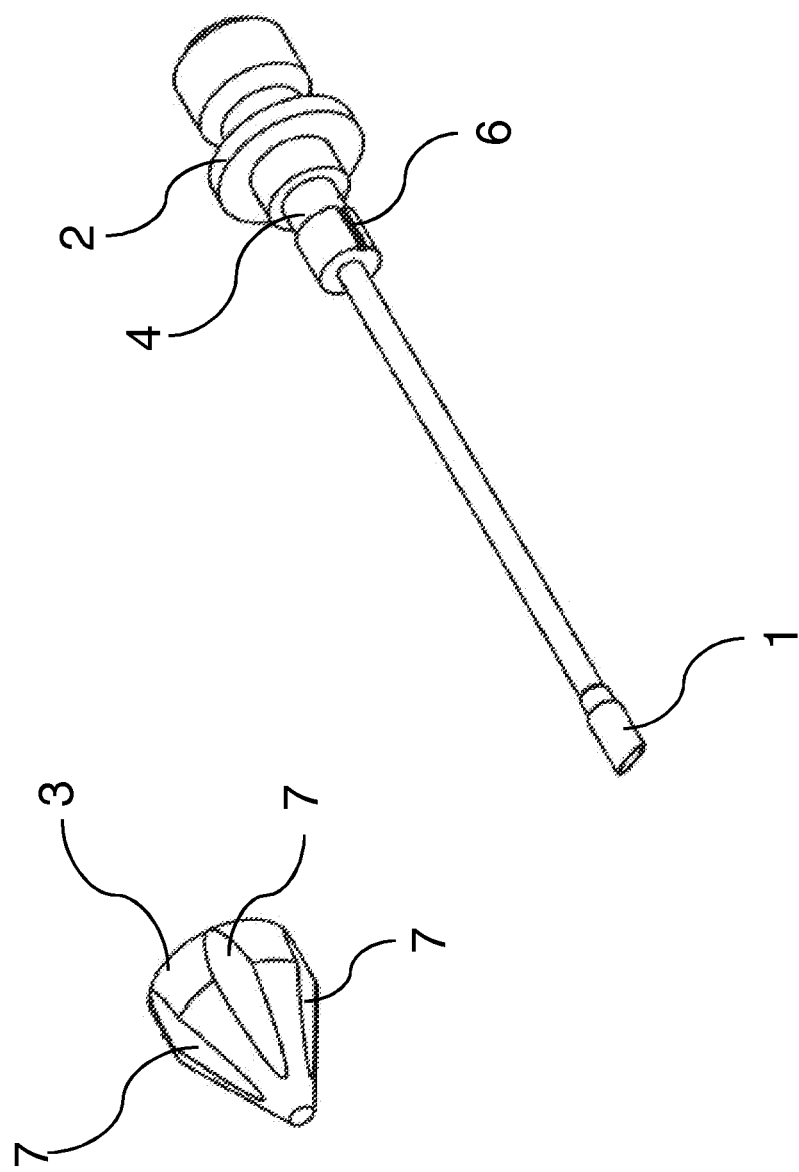

FIG. 3 shows the tool according to the invention from FIG. 1 in a perspective view, with the handling means 3 being shown detached from the connector part 2. FIG. 3 shows clearly that the handling means 3 completely surround the connector part 2 in a radial fashion. The handling means 3 are attached to the connector part 2 in an injection molding process and serve as an engagement point for a clamping tool 3.

The handling of the tool shall be explained in the following using the example of the hollow needle according to the invention shown in FIGS. 1 to 3. The operator selects the desired hollow needle, with the handling means 3 being of particular significance because they are used to code the hollow needle by virtue of their color or shape. Thus, the operator is able to recognize the "correct" needle from the handling means 3. The handling means 3 also obtain additional significance. The operator is able to discern by looking at the handling means 3 whether the tool has already been connected to a handle or has already been reprocessed or sterilized. If the properties of the handling means 3 do not show any changes, the hollow needle is screwed firmly onto the handle by its connector part 2. To this end, a clamping tool is used that engages in the depressions 7 of the handling means 3. The operator thus has the opportunity of determining in a simple manner whether the hollow needle has already been used, thus minimizing the risk to the patient of infection or injury to the greatest extent possible.

The object of the present invention is therefore to design and refine a medical tool of the type mentioned at the outset in such a way that, when handled in a simple fashion, safe functioning for the patient is guaranteed and the danger of cross-contamination is minimized. The further object of the invention is to provide a method for the production of such a medical tool.

The inventors recognized that the fundamental object can be attained in a surprisingly simple fashion by a clever design of the handling means. To this end, the handling means are designed in such a way that the properties of the handling means change upon connecting the tool to the handle or releasing the tool from the handle or when reprocessing the tool. Here, it should be noted that the term "properties" should be understood in its broadest sense, including any property of the handle that is perceptible to the user of the medical tool. This structure of the handling means obviates undesired multiple uses of the tool in an astoundingly simple manner. Changing the properties of the handle may be caused, for example, by connecting the tool to the handle or releasing the tool from the handle. Thus, it is automatically visible whether the tool has already been used. Moreover, the change to the handle may be caused by a reprocessing of the tool, regardless of the kind of reprocessing. The operator is constantly informed by the properties of the handling means whether the tool may be used for a medical intervention. The risk of infection and injury posed by the medical tool is reduced to a minimum by the design according to the invention.

From a structural viewpoint, it is particularly advantageous for the handling means to at least partially surround the connector part in a radial fashion. It is furthermore advantageous for the handling means to surround the connector part completely, such that the handling means are constantly visible independently of the radial orientation of the tool. Thus, the operator always has an ideal view of the handling means and their properties. A change to the properties is easy for the operator to recognize.

With regard to a secure connection between the handling means and the connector part, it is conceivable for the connector part to comprise a recess and the handling means to comprise a protrusion corresponding to the recess. The recess on the connector part may be embodied, for example, in the shape of a groove extending in the longitudinal direction of the tool. The protrusion of the handling means is then designed in a correspondingly elongated fashion and extends in the recess of the connector part. This structural measure allows the handling means to be disposed on the connector part in a rotationally secure fashion. Moreover, it is conceivable for the handling means to comprise a recess and for the connector part to comprise a protrusion corresponding to the recess. It is also possible for a plurality of recesses and protrusions having any desired geometry to be provided on the connector part and on the handling means. In order to secure the handling means in the longitudinal direction of the tool as well, the recess may be designed, for example, as a groove running around the connector part in a radial fashion.

It is advantageous for the handling means to be designed in such a way that their optical properties change upon processing and/or sterilization. Here, any type of reprocessing or sterilization is conceivable such as, for example, steam sterilization, hot-air sterilization, chemical sterilization, radiosterilizaiton, plasma sterilization, etc. To this end, the handling means may be made of a material that, for example, discernibly changes its color and/or transparency upon reprocessing. Any change to the optical properties of the handling means that is discernible to the operator is conceivable here. During surgical operation, it is thus also simple to determine whether the tool is being used for the first time. Moreover, it is conceivable for the handling means to be coated—for example, lacquered—with a material having the corresponding properties.

Moreover, the handling means can be embodied in such a way that they are damaged with the tool is reprocessed or sterilized. Any type of reprocessing or sterilization is conceivable here such as, for example, steam sterilization, hot-air sterilization, chemical sterilization, radiosterilizaiton, plasma sterilization, etc. For example, the handling means may be made of a material that melts when heated. This allows the operator to easily discern whether the tool has been used and reprocessed or sterilized. It is further conceivable for the handling means to be coated, for example, lacquered, with a material that has the corresponding properties. The use of reprocessed tools and the risks to the patient associated therewith is thus eliminated.

In order to be able to attach the tool to the handle as simply as possible, the handling means may serve as an engagement point for a clamping tool. To this end, the handling means may have a polygonal cross section, for example, the shape of a hexagonal nut. Moreover, the surface of the handling means may have a contour or recesses structured in any desired fashion, such that the clamping tool is able to engage with the handling means.

It is furthermore advantageous for the handling means to be designed in such a way that they are noticeably damaged by the clamping tool when connected to or released from the handle.

In order to simplify handling of the tool, it is particularly advantageous for the handling means to comprise a coding identifying the tool. The coding may be realized, for example, by a certain shape or geometry or a certain color of the handling means. Various geometries or different lumens of the tool may be designated in this manner with very little structural effort. Because these tools are often small, the handling of the tool is considerably simplified by coding the handling means.

It is particularly advantageous for the handling means to influence the oscillation behavior of the tool as an attenuator. If the tool is an instrument for ocular surgery, for example, that is subjected to ultrasound, the oscillation behavior can be influenced in a targeted fashion by the handling means.

The statements made above regarding the medical tool according to the invention also apply to the method according to the invention. To expand upon the statements made above, it should be mentioned that it is advantageous for the handling means to be attached to the finished connector part by injection molding or by means of a three-dimensional pressure method. The tool may, for example, initially be produced by machining or deformation and attached to the connector part and then the handling means. Here, the handling means are produced according to the invention in an injection molding process or by an "accretion" of material on the connector part. This produces a fixed connection between the handling means and the connector part such that the handling means cannot simply be disconnected from the connector part—particularly not without visible damage.

Finally, it should be explicitly mentioned that the exemplary embodiments of the device according to the invention described above serve only to explain the teaching claimed here, but do not limit said teaching to the exemplary embodiments.

LIST OF REFERENCE CHARACTERS

1 Functional part
2 Connector part
3 Handling means
4 First recess
5 First protrusion
6 Second recess
7 Depression

The invention claimed is:

1. A hollow needle for an instrument used in ocular surgery for in-vivo disintegration of organic lenses by means of ultrasound, said needle comprising:
   a functional part (1); and
   a connector part (2), the connector part (2) comprising handling means (3) and serving to form a detachable connection with a handle,
   wherein:
      the properties of the handling means (3) change upon at least one of connection of the needle to the handle or removal of the needle from the handle;
      the handling means (3) are embodied as an engagement point for a clamping tool;
      the clamping tool visibly damages the handling means (3) upon at least one of connection of the needle to the handle or disconnection of the needle from the handle,
   wherein said visible damage is perceptible to a user of the instrument;
      the connector part (2) further comprises a circumferential groove (4) and an axial groove (6); and
      the handling means (3) further comprises a circumferential protrusion and an axial protrusion that engage with said circumferential groove (4) and said axial groove (6), respectively, so as to securely fasten said handling means (3) to said connector part (2).

2. The needle according to claim 1, wherein the handling means (3) at least partially surround the connector part (2) in a radial fashion.

3. The needle according to claim 1, wherein the handling means (3) are made of a material whose optical properties change upon at least one of reprocessing or sterilization of the needle.

4. The needle according to claim 3, wherein the material is at least one of a plastic or a resin.

5. The needle according to claim 3, wherein the optical properties comprise at least one of color or transparency.

6. The needle according to claim 1, wherein the handling means (3) are coated with a material whose optical properties change upon at least one of reprocessing or sterilization of the needle.

7. The needle according to claim 6, wherein the material is at least one of a plastic or a resin.

8. The needle according to claim 6, wherein the optical properties comprise at least one of color or transparency.

9. The needle according claim 1, wherein the handling means (3) are made of a material that is damaged upon at least one of a reprocessing or sterilization of the needle.

10. The needle according to claim 9, wherein the material is at least one of a plastic or a resin.

11. The needle according to claim 9, wherein the material melts upon the reprocessing or sterilization of the tool.

12. The needle according to claim 1, wherein the handling means (3) are coated with a material that is damaged upon at least one of a reprocessing or sterilization of the needle.

13. The needle according to claim 12, wherein the material is at least one of a plastic or a resin.

14. The needle according to claim 12, wherein the material melts upon the reprocessing or sterilization of the needle.

15. The needle according to claim 1, wherein the engagement point comprises a polygonal cross section of the handling means (3).

16. The needle according to claim 1, wherein the handling means (3) comprise a coding identifying the needle.

17. The needle according to claim 16, wherein the coding identifying the needle comprises at least one of a certain color or a certain geometry.

18. The needle according to claim 1, wherein the handling means (3) influence the oscillation behavior of the needle as an attenuator.

19. A method for the production of a hollow needle according to claim 1 and for an instrument used in ocular surgery for the in-vivo disintegration of organic lenses by means of ultrasound, said method comprising the steps of:
   providing a hollow needle, said hollow needle having a functional part (1) and a connector part (2), with the connector part (2) comprising handling means (3), wherein the handling means (3) are embodied as an engagement point for a clamping tool and serve to connect the tool to a handle in a detachable fashion, wherein the clamping tool visibly damages the handling means (3) upon at least one of connection of the needle to the handle or disconnection of the needle from the handle, said visible damage being perceptible to a user of the instrument, wherein the properties of the handling means (3) change upon connection of the needle to the handle or removal of the needle from the handle, wherein the connector part (2) further comprises a circumferential groove (4) and an axial groove (6), and wherein the handling means (3) further comprises a circumferential protrusion and an axial protrusion that engage with said circumferential groove (4)

and said axial groove (6), respectively, so as to securely fasten said handling means (3) to said connector part (2); and further attaching the handling means (3) to a finished connector part (2) by injection molding or by means of a three-dimensional pressure method.

* * * * *